United States Patent
Nesvadba et al.

(10) Patent No.: US 10,113,075 B2
(45) Date of Patent: Oct. 30, 2018

(54) POLYCYCLIC PHOTOINITIATORS

(71) Applicant: IGM Malta Limited, Gzira GZR (MT)

(72) Inventors: Peter Nesvadba, Marly (CH); Lucienne Bugnon Folger, Pfeffingen (CH); Antoine Carroy, Limburgerhof (DE)

(73) Assignee: IGM Malta Limited (MT)

( * ) Notice: Subject to any disclaimer, the term of this patent is extended or adjusted under 35 U.S.C. 154(b) by 0 days.

(21) Appl. No.: 15/506,852

(22) PCT Filed: Aug. 13, 2015

(86) PCT No.: PCT/IB2015/056178
§ 371 (c)(1),
(2) Date: Feb. 27, 2017

(87) PCT Pub. No.: WO2016/034963
PCT Pub. Date: Mar. 10, 2016

(65) Prior Publication Data
US 2017/0240755 A1    Aug. 24, 2017

(30) Foreign Application Priority Data
Sep. 4, 2014    (EP) .................................. 14183473

(51) Int. Cl.
| C08F 2/46 | (2006.01) |
| C08F 2/50 | (2006.01) |
| C08G 61/04 | (2006.01) |
| C09D 11/101 | (2014.01) |
| C07D 311/82 | (2006.01) |
| C07D 307/91 | (2006.01) |
| C07D 327/08 | (2006.01) |
| C07D 339/08 | (2006.01) |
| C08L 33/14 | (2006.01) |
| C09D 133/14 | (2006.01) |
| C09D 11/107 | (2014.01) |

(52) U.S. Cl.
CPC .......... *C09D 11/101* (2013.01); *C07D 307/91* (2013.01); *C07D 311/82* (2013.01); *C07D 327/08* (2013.01); *C07D 339/08* (2013.01); *C08L 33/14* (2013.01); *C09D 11/107* (2013.01); *C09D 133/14* (2013.01)

(58) Field of Classification Search
None
See application file for complete search history.

(56) References Cited

U.S. PATENT DOCUMENTS

| 3,859,286 A | 1/1975 | Fleming et al. |
| 3,937,835 A | 2/1976 | Shemano |
| 3,957,989 A | 5/1976 | Fleming et al. |
| 4,496,447 A | 1/1985 | Eichler et al. |
| 4,559,371 A * | 12/1985 | Husler .................... C07C 45/46 |
| | | 106/31.43 |
| 4,575,330 A | 3/1986 | Hull |

(Continued)

FOREIGN PATENT DOCUMENTS

| CN | 1942461 A | 4/2007 |
| CN | 101941920 A | 1/2011 |

(Continued)

OTHER PUBLICATIONS

Tsushima et al, JP 2008-031280 Machine Translation, Feb. 14, 2008 (Year: 2008).*

(Continued)

*Primary Examiner* — Jessica Whiteley
(74) *Attorney, Agent, or Firm* — Tarolli, Sundheim, Covell & Tummino LLP

(57) ABSTRACT

Compounds of the formula (I) (I), wherein X is O, S, a direct bond or $CR_{16}R_{17}$; Y is O or S; $R_1$, $R_2$, $R_3$, $R_4$, $R_5$, $R_6$, $R_7$ and $R_8$ for example are hydrogen, halogen, $C_1$-$C_4$alkyl, or a group of formula (II) or (III) (II) (III) provided that either (i) one of $R_1$, $R_2$, $R_3$, $R_4$, $R_5$, $R_6$, $R_7$ or $R_8$ is a group of formula (II) or (III); or (ii) one of $R_1$, $R_2$, $R_3$ or $R_4$ is a group of formula (II) or (III) and one of $R_5$, $R_6$, $R_7$ or $R_8$ is a group of formula (II) or (III); $R_9$ and $R_{10}$ independently of each other are $C_1$-$C_4$alkyl or together with the C atom to which they are attached form a 5-membered, 6-membered or 7-membered carbocyclic ring; $R_{11}$ is hydrogen, $C_1$-$C_4$alkyl, $C_5$-$C_7$cycloalkyl, 2-tetrahydropyranyl or $Si(C_1$-$C_4$alkyl$)_3$; $R_{12}$ and $R_{13}$ for example are $C_1$-$C_4$alkyl, $C_2$-$C_{12}$alkenyl, phenyl-$C_1$-$C_4$alkyl, phenyl-$C_1$-$C_4$alkyl which is substituted by $C_1$-$C_4$alkyl, $R_{14}$ and $R_{15}$ independently of each other are $C_1$-$C_4$alkyl, $C_5$-$C_7$cycloalkyl, or together with the N atom to which they are attached form a 5-membered, 6-membered or 7-membered ring, which may contain additional heteroatoms O, S or N; $R_{16}$ and $R_{17}$ for example are hydrogen, $C_1$-$C_5$alkyl, $C_5$-$C_7$cycloalkyl, phenyl-$C_1$-$C_4$alkyl, phenyl; are effective photoinitiators.

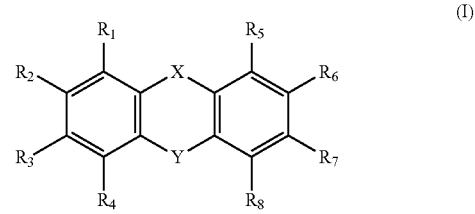

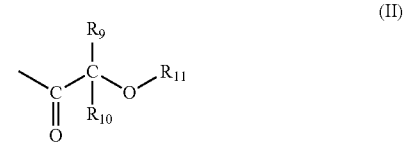

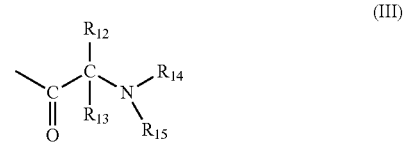

5 Claims, No Drawings

(56) References Cited

U.S. PATENT DOCUMENTS

| | | | |
|---|---|---|---|
| 4,582,862 A | 4/1986 | Berner et al. | |
| 4,950,581 A | 8/1990 | Koike et al. | |
| 5,013,768 A | 5/1991 | Kiriyama et al. | |
| 5,077,402 A | 12/1991 | Desobry et al. | |
| 5,376,459 A | 12/1994 | Christner et al. | |
| 5,795,985 A | 8/1998 | Husler et al. | |
| 5,977,357 A | 11/1999 | Husler et al. | |
| 6,191,182 B1 | 2/2001 | Husler et al. | |
| 7,084,183 B2 | 8/2006 | Fuchs et al. | |
| 2001/0027253 A1* | 10/2001 | Hall-Goulle | C07D 487/04 544/235 |

FOREIGN PATENT DOCUMENTS

| | | |
|---|---|---|
| DE | 2308830 A1 | 8/1974 |
| DE | 4013358 A1 | 10/1991 |
| DE | 4228514 A1 | 3/1994 |
| DE | 19700064 A1 | 7/1997 |
| EP | 0007086 A1 | 1/1981 |
| EP | 041125 A1 | 12/1981 |
| EP | 0088050 A2 | 9/1983 |
| EP | 0117233 A1 | 8/1984 |
| EP | 0138754 A2 | 4/1985 |
| EP | 245639 A2 | 11/1987 |
| EP | 0284561 A2 | 9/1988 |
| EP | 339841 A2 | 11/1989 |
| EP | 438123 A2 | 7/1991 |
| EP | 445624 A2 | 9/1991 |
| EP | 636669 A1 | 2/1995 |
| EP | 678534 A1 | 10/1995 |
| GB | 2180358 A | 3/1987 |
| JP | S58157805 A | 9/1983 |
| JP | S59167546 A | 9/1984 |
| JP | S6084248 A1 | 5/1985 |
| JP | S63264560 A | 11/1988 |
| JP | H06-68309 A | 3/1994 |
| JP | 10-287450 A | 10/1998 |
| JP | 2007-535506 A | 12/2007 |
| JP | 2008-031280 * | 2/2008 |
| JP | 2010-024291 * | 2/2010 |
| JP | 2013-148872 A | 8/2013 |
| WO | 90/01512 A1 | 8/1988 |
| WO | 03/064061 A1 | 8/2003 |
| WO | 04/074328 A1 | 9/2004 |
| WO | 2005/105772 A1 | 11/2005 |
| WO | 06/008251 A2 | 1/2006 |
| WO | 2006/005682 A2 | 1/2006 |

OTHER PUBLICATIONS

Matsumura, JP 2010-024291 Machine Translation, Feb. 4, 2010 (Year: 2010).*

Schut, Jan H., "Is dry paint in your future", Plastics world vol. 54, No. 7, pp. 48-52, Jul. 1996.

Sengul, et al., "Synthesis of macrocyclic systems derived from di-(2-indolyl)heteroarenes", Tetrahedron 68, pp. 9050-9055, 2012.

Coic, et al., "Meso Heterocyclic Analogues of 9, 10-Dihydroanthracene. XIII. On the Structure of the Products of Diacelyation of Phenoxathiin: A correction (1)", Journal of Heterocyclic Chemistry vol. 15, No. 5, pp. 769-772, 1978.

Bianco, et al., "Synthesis of 2-Hyrdoxyacetyl-7-Acetyk-Xanthone, a New Xanthone Derivative Endowed with Antianaphylactic, Analgesic, and Atiinflammatory Activities", IL Farmaco vol. 44, No. 6, pp. 547-554, 1989.

Bertsch, et al., "Study of the spatial resolution of a new 3D microfabrication process: the microstereophitilithography using a dynamic mask-generator technique", Journal of Photochemistry and Photobiology A, 107, pp. 275-281, 1997.

First Office Action for Japanese Application No. 2017-512391, dated Mar. 14, 2018.

Extended European Search Report for Patent Application No. 15838639.1-1110/3189083, dated Mar. 19. 2018.

Ortega, et al., "Enhanced Resistance to Experimental Systemic Candidiasis in Tilorone-Treated Mice", FEMS Immunology and Medical Microbiology, 28, 2000, pp. 283-289.

Levine, et al., "T-Lymphocyte depletion induced in rats by analogs of tilorone hydrochloride", Toxicology and Applied Pharmacology, vol. 40, Issue 1, Apr. 1977, pp. 137-145—Abstract.

* cited by examiner

POLYCYCLIC PHOTOINITIATORS

Object of the present invention are photopolymerizable compositions comprising polycyclic photoinitiators for polymerization (curing) of radically polymerizable compositions triggered by electromagnetic radiation, as well as novel polycyclic photoinitiator compounds.

Radiation curing of large variety of radically polymerizable compositions is a well-known technique and α-hydroxyketone and α-aminoketone compounds are well-known photoinitiators for radiation curing.

Such compounds are for example described in U.S. Pat. No. 5,077,402, U.S. Pat. No. 4,559,371, U.S. Pat. No. 4,582,862, U.S. Pat. No. 7,084,183. In U.S. Pat. No. 3,957,989, U.S. Pat. No. 3,937,835 and in Toxicology and Applied Pharmacology 40, 1977, pages 137-145, several amino-substituted polycyclic compounds are disclosed for pharmaceutical applications.

The increasing concerns about health and environmental aspects of chemicals require replacement of volatile photoinitiators with new ones having lower volatility and higher activity.

Typically, the α-hydroxyketone or α-aminoketone functional group in these established photoinitiators is attached to a monocyclic aromatic ring, most often benzene ring which may bear some addition substituents to adjust ancillary properties of these photoinitiators (e.g. volatility, position of the absorption maxima).

We have now discovered that polycyclic α-hydroxyketones and α-aminoketones represent highly efficient photoinitiators with low volatility and outstanding curing properties. Surprisingly, photoinitiators in which one or several α-hydroxyketone or α-aminoketone functional group is attached to a polycyclic aromatic or heteroaromatic system are very efficient. Therefore, the subject of the present invention are photopolymerizable compositions comprising
(A) at least one ethylenically unsaturated photopolymerizable compound and
(B) at least one photoinitiator compound of formula (I)

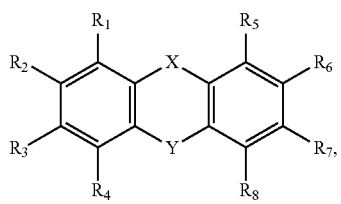

(I)

X is O, S, a direct bond or $CR_{16}R_{17}$;
Y is O or S;
$R_1$, $R_2$, $R_3$, $R_4$, $R_5$, $R_6$, $R_7$ and $R_8$ independently of each other are hydrogen, halogen, $C_1$-$C_4$alkyl, $C_5$-$C_7$cycloalkyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (II) or (III)

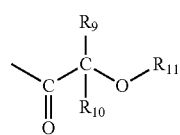

(II)

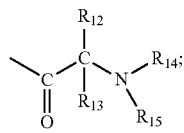

(III)

provided that
either
(i) one of $R_1$, $R_2$, $R_3$, $R_4$, $R_5$, $R_6$, $R_7$ or $R_8$ is a group of formula (II) or (III); or
(ii) one of $R_1$, $R_2$, $R_3$ or $R_4$ is a group of formula (II) or (III) and one of $R_5$, $R_6$, $R_7$ or $R_8$ is a group of formula (II) or (III);
$R_9$ and $R_{10}$ independently of each other are $C_1$-$C_4$alkyl or together with the C atom to which they are attached form a 5-membered, 6-membered or 7-membered carbocyclic ring;
$R_{11}$ is hydrogen, $C_1$-$C_4$alkyl, $C_5$-$C_7$cycloalkyl, 2-tetrahydropyranyl or $Si(C_1$-$C_4alkyl)_3$;
$R_{12}$ and $R_{13}$ independently of each other are $C_1$-$C_4$alkyl, $C_2$-$C_{12}$alkenyl, phenyl-$C_1$-$C_4$alkyl, phenyl-$C_1$-$C_4$alkyl which is substituted by $C_1$-$C_4$alkyl, or $R_{12}$ and $R_{13}$ together with the C atom to which they are attached form a 5-membered, 6-membered or 7-membered carbocyclic ring;
$R_{14}$ and $R_{15}$ independently of each other are $C_1$-$C_4$alkyl, $C_5$-$C_7$cycloalkyl, or together with the N atom to which they are attached form a 5-membered, 6-membered or 7-membered ring, which may contain additional heteroatoms O, S or N;
$R_{16}$ and $R_{17}$ independently of each other are hydrogen, $C_1$-$C_8$alkyl, $C_5$-$C_7$cycloalkyl, phenyl-$C_1$-$C_4$alkyl, phenyl or together with the C atom to which they are attached form a 5-membered, 6-membered or 7-membered ring;
provided that
(1) compounds wherein $R_2$ is a group of formula (III) and $R_{14}$ and $R_{15}$ together with the N atom to which they are attached form a 6-membered ring, which contains an additional heteroatom O, X is a direct bond and Y is O; and
(2) compounds wherein $R_2$ is a group of formula (III) and $R_{14}$ and $R_{15}$ together with the N atom to which they are attached form a 6-membered ring, which contains an additional heteroatom O and X and Y are S; and
(3) compounds wherein $R_7$ is a group of formula (III) and $R_{14}$ and $R_{15}$ together with the N atom to which they are attached form a 6-membered ring, which contains an additional heteroatom O and X and Y are S;
are excluded.

A further subject of the invention are novel photoinitiator compounds of the formula (I")

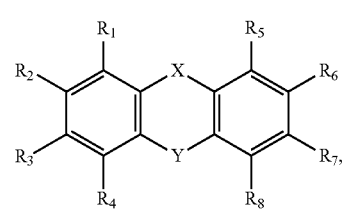

(I")

X is O, S, a direct bond or $CR_{16}R_{17}$;
Y is O or S;
$R_1$, $R_2$, $R_3$, $R_4$, $R_5$, $R_6$, $R_7$ and $R_8$ independently of each other are hydrogen, halogen, $C_1$-$C_4$alkyl, $C_5$-$C_7$cycloalkyl, phenyl, $C_1$-$C_4$alkoxy, $C_5$-$C_7$cycloalkoxy, phenoxy, $C_1$-$C_4$-alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (II)

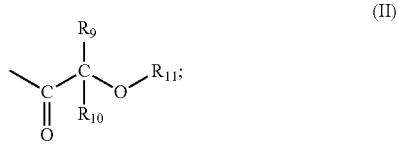

(II)

$R_9$ and $R_{10}$ independently of each other are $C_1$-$C_4$alkyl or together with the C atom to which they are attached form a 5-membered, 6-membered or 7-membered carbocyclic ring; $R_{11}$ is hydrogen, $C_1$-$C_4$alkyl, $C_5$-$C_7$cycloalkyl, 2-tetrahydropyranyl or Si($C_1$-$C_4$alkyl)$_3$.

The following explanations and preferences apply for both, the compounds of the formula (I) and the ones of the formula (I").

$C_1$-$C_8$alkyl is linear or branched and is, for example $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2, 4,4-trimethylpentyl, 2-ethylhexyl or n-octyl.

$C_1$-$C_4$alkyl has the same meanings as given above up to the corresponding number of C-atoms.

$C_5$-$C_7$cycloalkyl is for example cyclopropyl, cyclopentyl, cyclohexyl or cycloheptyl, especially cyclopentyl and cyclohexyl, preferably cyclohexyl.

$C_1$-$C_4$alkoxy is linear or branched and is for example methoxy, ethoxy, propoxy, isopropoxy, n-butyloxy, sec-butyloxy, iso-butyloxy or tert-butyloxy, especially methoxy.

$C_5$-$C_7$cycloalkoxy is $C_5$-$C_7$cycloalkyl-O—, wherein the $C_5$-$C_7$cycloalkyl is defined as given above.

$C_2$-$C_{12}$alkenyl radicals are mono or polyunsaturated, linear or branched and are for example $C_2$-$C_8$-, $C_2$-$C_6$- or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_1$-$C_4$alkylthio is linear or branched and is for methylthio, ethylthio, propylthio, isopropylthio, n-butylthio, sec-butylthio, iso-butylthio or tert-butylthio, preferably methylthio.

The $C_1$-$C_4$alkyl and the $C_5$-$C_7$cycloalkyl in the terms di($C_1$-$C_4$alkyl)amino, Si($C_1$-$C_4$alkyl)$_3$ $C_5$-$C_7$cycloalkylthio, and di($C_5$-$C_7$cycloalkyl)amino have the meanings as given above. Halogen is fluorine, chlorine, bromine and iodine, especially fluorine, chlorine and bromine, preferably fluorine and chlorine.

If $R_9$ and $R_{10}$ or $R_{12}$ and $R_{13}$ together with the C atom to which they are attached form a 5-membered, 6-membered or 7-membered carbocyclic ring, preferably a saturated carbocyclic ring, structures like e.g.

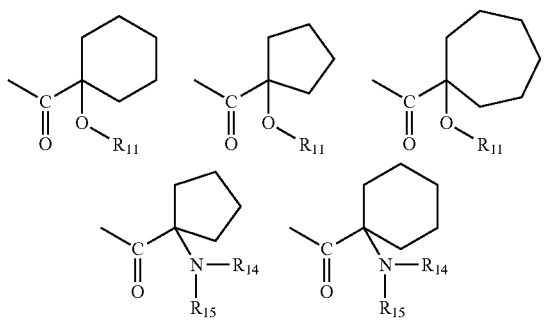

are formed.

If $R_{14}$ and $R_{15}$ together with the N atom to which they are attached form a 5-membered, 6-membered or 7-membered ring, which may contain additional heteroatoms O or N, saturated or unsaturated rings are formed, for example aziridine, pyrrole, pyrrolidine, oxazole, pyridine, 1,3-diazine, 1,2-diazine, piperidine or morpholine. Preferably piperidine or morpholine, in particular morpholine.

If $R_{16}$ and $R_{17}$ together with the C atom to which they are attached form a 5-membered, 6-membered or 7-membered ring, preferably a saturated ring, structures like e.g.

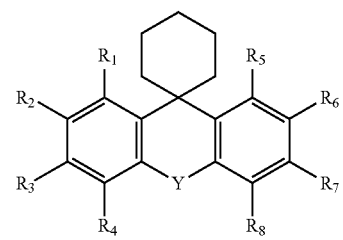

are formed.

If $R_{14}$ and $R_{15}$ together with the N atom to which they are attached form a 5-membered, 6-membered or 7-membered ring, which may contain additional heteroatoms O, S or N, saturated or unsaturated rings are formed, for example aziridine, pyrrole, pyrrolidine, oxazole, pyridine, 1,3-diazine, 1,2-diazine, piperidine or morpholine, in particular morpholine.

The terms "and/or" or "or/and" in the present context are meant to express that not only one of the defined alternatives (substituents) may be present, but also several of the defined alternatives (substituents) together, namely mixtures of different alternatives (substituents).

The term "optionally substituted" means, that the radical to which it refers is either unsubstituted or substituted.

The term "at least" is meant to define one or more than one, for example one or two or three, preferably one or two.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The term "(meth)acrylate" in the context of the present application is meant to refer to the acrylate as well as to the corresponding methacrylate.

The preferences indicated above for the compounds according to the present invention in the context of this invention are intended to refer to all categories of the claims, that is to the compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The compounds of the present invention can be made by methods well established for the synthesis of α-hydroxyketone and α-aminoketone photoinitiators.

One, non limiting possibility consists of Friedel-Crafts acylation of a polycyclic heterocyclic compound with a suitable acid derivative (e.g. acid halide or anhydride) to afford the corresponding mono- or di-acylated heterocyclic compound. Friedel-Crafts acylations on the polycyclic heterocyclic systems which are pertinent to the present invention are well known. These acylations can be regioselective or can afford a mixtures of regioisomers. For examples, acylations of xanthenes proceed regioselectively to afford the 2-acyl- or 2,7-diacyl derivatives (see e.g. Bianco, A. et al, *Farmaco* (1989), 44(6), 547-54).

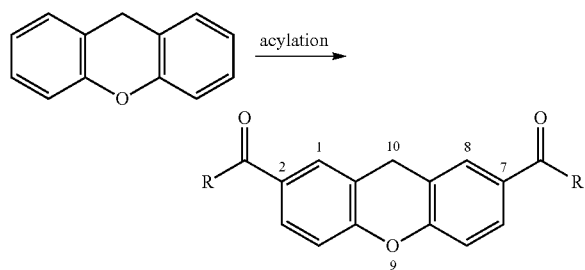

Regioselective acylation is reported to occur also with dibenzofurane to afford 2-acyl or 2,8-diacyl derivatives (see e.g. Sengul, Ibrahim F. et al, *Tetrahedron* (2012), 68(44), 9050-9055).

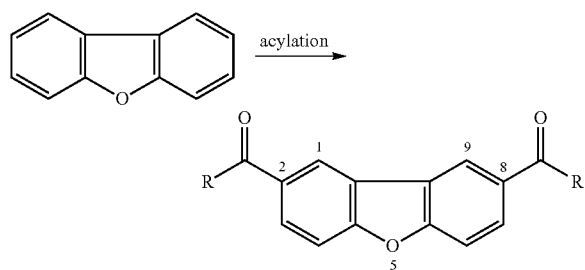

On the other hand, a mixture of 2- and 3-monoacyl- or 2,7- and 2,8-diacyl derivatives is obtained upon Friedel-Craft acylation of phenoxathiin (see e.g. Coic, J. P. et al., *Journal of Heterocyclic Chemistry* (1978), 15(5), 769-72).

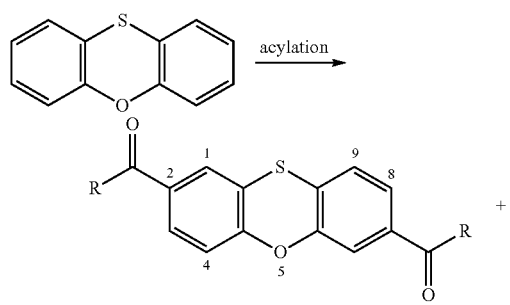

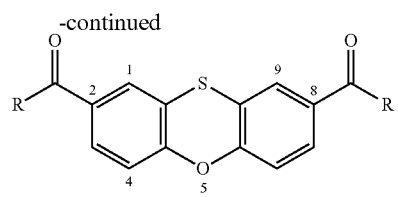

Thus, the outcome of the Friedel-Crafts diacylation in the other cases pertinent to this invention may be a single regioisomer or a mixture of 2 or even more regioisomers. Accordingly, subject of the invention are the single regioisomers as well as the mixture of isomers.

The transformation of the mono- or diacylated polycyclic heterocyclic compound into the corresponding α-hydroxyketone and α-aminoketone is well known and can be performed by variety of methods.

One possible, non limiting approach to α-hydroxyketones consists of α-halogenation of the acylated polycyclic heterocyclic compound followed by substitution of the halogen with OH. Halogenation is performed for example with $Cl_2$, $Br_2$ or $SO_2Cl_2$. The substitution of the halogen can be achieved with water or with aqueous solutions of alkali hydroxides or carbonates.

This approach is exemplified in examples 1-5.

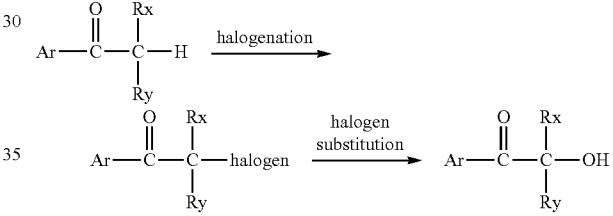

Another possible approach to α-hydroxyketones consists of reaction of the α-halogenated acylated compound with an alkoholate to afford an alkoxy-oxirane intermediate, followed by opening of its ring with water or with aqueous acid or base.

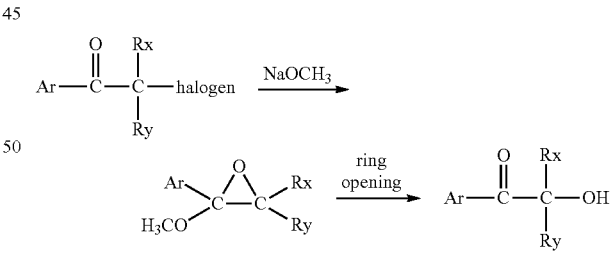

These reactions are known to the person skilled in the art and for example described in U.S. Pat. No. 4,318,791.

Yet another possibility consists of halomethylation, for example chloromethylation with formaldehyde and HCl, of the polycyclic heterocyclic compound. Subsequent reaction of the halomethylated compound with a dialkylsulfide, for example with tetrahydrothiophene, affords the sulfonium salt which is converted into an oxirane through reaction with a ketone and base. Hydrolytic ring opening of the oxirane affords the diol compound which is then oxidized into the desired α-hydroxyketone. The appropriate reaction conditions for this synthesis are described in WO2006/005682.

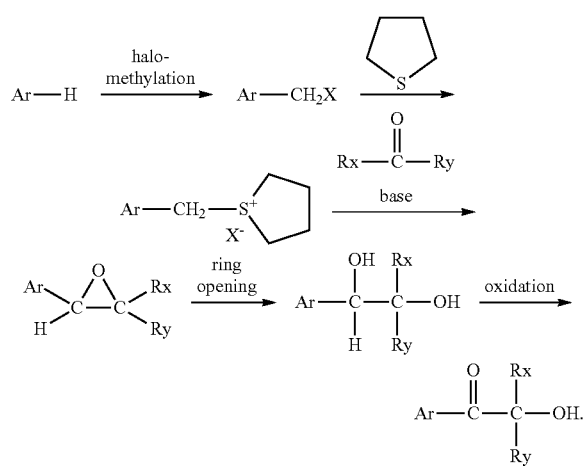

Subject of the invention also is a process for the preparation of a compound of the formula (I") by
1 Friedel-Crafts acylation of a polycyclic aryl compound

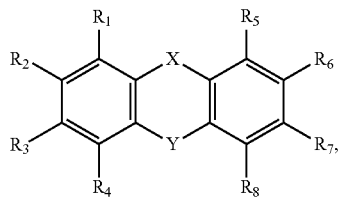

wherein
R$_1$, R$_2$, R$_3$, R$_4$, R$_5$, R$_6$, R$_7$ and R$_8$ independently of each other are hydrogen, halogen, C$_1$-C$_4$alkyl, C$_5$-C$_7$cycloalkyl, phenyl, C$_1$-C$_4$alkoxy, C$_5$-C$_7$cycloalkoxy, phenoxy, C$_1$-C$_4$alkylthio, C$_5$-C$_7$cycloalkylthio, phenylthio, di(C$_1$-C$_4$alkyl)amino, di(C$_5$-C$_7$cycloalkyl)amino, N-morpholinyl, N-piperidinyl,
provided that at least one of R$_1$, R$_2$, R$_3$, R$_4$, R$_5$, R$_6$, R$_7$ and R$_8$ is hydrogen; and X is O, S, a direct bond or CR$_{16}$R$_{17}$, and Y is O or S;
with a halogenide compound (IIa) or an anhydride compound (IVa)

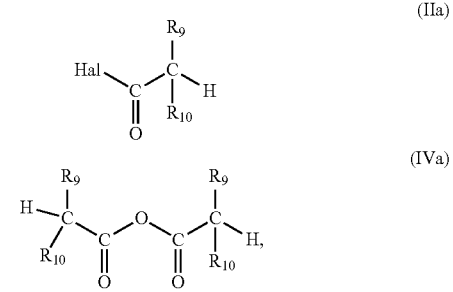

R$_9$ and R$_{10}$ are independently of each other are C$_1$-C$_4$ alkyl or together the C atom to which they are attached form a 5-membered, 6-membered or 7-membered carbocyclic ring; and Hal is halogenide, prefereable chloride;

2 subsequent halogenation, in particular bromination, of the resulting Friedel-Crafts adduct;
3 hydrolysis of the halogenated intermediate to give the corresponding α-hydroxyketone compound of the formula (I").

The α-aminoxyketones can be prepared from the same intermediates which are used for the synthesis of the α-hydroxyketones.

Thus, direct replacement of the halogen in the α-halogenated acylated compound with the amine NHR$_{14}$R$_{15}$ is possible in some cases.

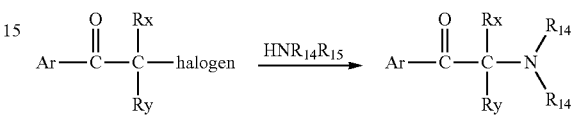

The alkoxy-oxiranes afford the α-aminoxyketones upon reaction with amines NHR$_{14}$R$_{15}$. This approach is exemplified in examples 6-7.

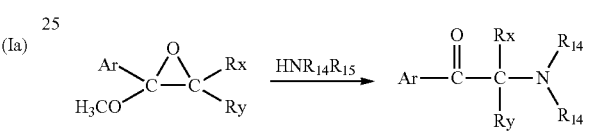

Similarly, the oxiranes obtained by the sulfide route described in WO2006/005682 can be opened by the amines and the resulting aminoalcohols can be further oxidized into the corresponding α-aminoxyketones

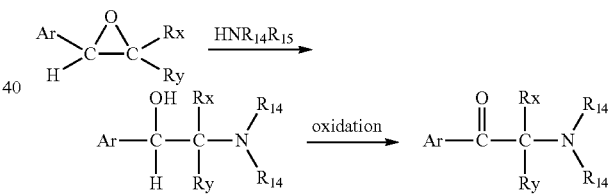

α-Aminoketones also may be prepared according to the method described in U.S. Pat. No. 5,977,357, U.S. Pat. No. 5,795,985 and U.S. Pat. No. 6,191,182. It consists of acylation of the polycyclic heteroaromatic compound with a suitable derivative of the acid R$_{12}$CH$_2$COOH, halogenation of the acyl-derivative, aminolysis of the halogenated compound with the amine HNR$_{14}$R$_{15}$ followed by quaternization to introduce the group R$_{13}$ and Stevens-rearrangement of the quarternary salt.

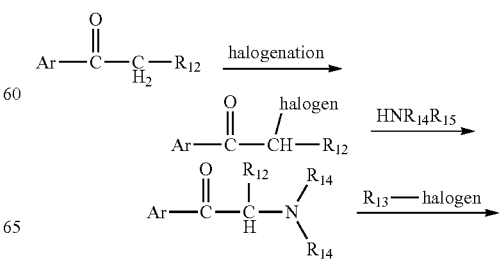

-continued

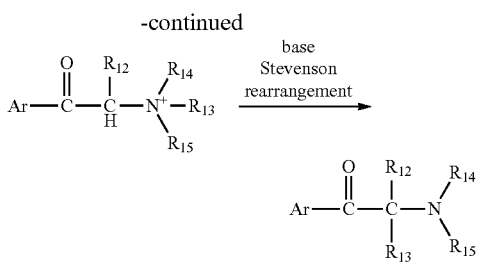

These reactions are well-known and the corresponding reaction conditions can be found in the cited documents.

In the above reaction schemes in the formulae Ar denotes the polycyclic aryl ring of the compounds according to the invention, $R_x$ and $R_y$ refer to $R_9$ and $R_{10}$ or $R_{12}$ and $R_{13}$, respectively, X is halogen, while $R_9$, $R_{10}$, $R_{12}$, $R_{13}$, $R_{14}$ and $R_{15}$ are as defined above in the definition for formula (I).

Many of the polycyclic aryl intermediates to be acylated and then transformed into the α-hydroxy ketones or α-amino ketones according to the invention are commercially available.

Interesting are compounds of the formula (I) or (I"), wherein
(i) one of $R_1$, $R_2$, $R_3$, $R_4$, $R_5$, $R_6$, $R_7$ or $R_8$ is a group of formula (II);
or
(ii) one of $R_1$, $R_2$, $R_3$ or $R_4$ is a group of formula (II) and one of $R_5$, $R_6$, $R_7$ or $R_8$ is a group of formula (II).

In particular interesting are compounds of the formula (I) or (I"), wherein
(i) one of $R_1$, $R_2$, $R_3$, $R_4$, $R_5$, $R_6$, $R_7$ or $R_8$ is a group of formula (II);
or
(ii) one of $R_1$, $R_2$, $R_3$ or $R_4$ is a group of formula (II) and one of $R_5$, $R_6$, $R_7$ or $R_8$ is a group of formula (II);
$R_9$ and $R_{10}$ are methyl or together with the C atom to which they are attached form a 6-membered carbocyclic ring; and $R_{11}$ is hydrogen.

Further emphasis is laid on compounds of the formula (I) as described above, wherein the remaining groups $R_1$ to $R_4$ and $R_5$ to $R_8$ are independently hydrogen, halogen, $C_1$-$C_4$alkyl, $C_1$-$C_4$alkoxy, $C_1$-$C_4$alkylthio, N-morpholinyl or N-piperidinyl.

In particular the remaining groups $R_1$ to $R_4$ and $R_5$ to $R_8$ are hydrogen.

Interesting further are compounds of the formula (I), wherein
(i) one of $R_1$, $R_2$, $R_3$, $R_4$, $R_5$, $R_6$, $R_7$ or $R_8$ is a group of formula (III); or
(ii) one of $R_1$, $R_2$, $R_3$ or $R_4$ is a group of formula (III) and one of $R_5$, $R_6$, $R_7$ or $R_8$ is a group of formula (III).

Of particular interest are compounds of the formula (I), wherein
(i) one of $R_1$, $R_2$, $R_3$, $R_4$, $R_5$, $R_6$, $R_7$ or $R_8$ is a group of formula (III); or
(ii) one of $R_1$, $R_2$, $R_3$ or $R_4$ is a group of formula (III) and one of $R_5$, $R_6$, $R_7$ or $R_8$ is a group of formula (III);
$R_{12}$ and $R_{13}$ are $C_1$-$C_2$alkyl or benzyl; and
$R_{14}$ and $R_{15}$ are $C_1$-$C_4$alkyl or together with the N atom to which they are attached form a 6-membered ring, which may contain additional heteroatoms O or N.

Further emphasis is laid on compounds of the formula (I) or (I") as described above, wherein
the remaining groups $R_1$ to $R_4$ and $R_5$ to $R_8$ are independently hydrogen, halogen, $C_1$-$C_4$alkyl, $C_1$-$C_4$alkoxy, $C_1$-$C_4$alkylthio, N-morpholinyl or N-piperidinyl.

In particular the remaining groups $R_1$ to $R_4$ and $R_5$ to $R_8$ are hydrogen.

Further interesting are photopolymerizable compositions comprising photoinitiator compounds of the formula (I), wherein one of $R_1$, $R_2$, $R_3$ or $R_4$ or one of $R_5$, $R_6$; $R_7$ or $R_8$ is a group of the formula (II) or (III).

Interesting further are photopolymerizable compositions comprising photoinitiator compounds of the formula (I"), wherein one of $R_1$, $R_2$, $R_3$ or $R_4$ or one of $R_5$, $R_6$; $R_7$ or $R_8$ is a group of the formula (II).

Emphasis has to be laid on photopolymerizable compositions comprising photoinitiator compounds of the formula (I), wherein one of $R_1$, $R_2$, $R_3$ or $R_4$ and one of $R_5$, $R_6$, $R_7$ or $R_8$ is a group of the formula (II) or (III).

Interesting further are photopolymerizable compositions comprising at photoinitiator compounds of the formula (I"), wherein one of $R_1$, $R_2$, $R_3$ or $R_4$ and one of $R_5$, $R_6$, $R_7$ or $R_8$ is a group of the formula (II)

In particular interesting are photopolymerizable compositions comprising photoinitiator compounds of the formula (I), wherein
one of $R_1$, $R_2$, $R_3$ or $R_4$ and one of $R_5$, $R_6$, $R_7$ or $R_8$ is a group of the formula (II); or one of $R_1$, $R_2$, $R_3$ or $R_4$ and one of $R_5$, $R_6$, $R_7$ or $R_8$ is a group of the formula (III).

Interesting further are photopolymerizable compositions comprising at photoinitiator compounds of the formula (I"), wherein one of $R_1$, $R_2$, $R_3$ or $R_4$ and one of $R_5$, $R_6$, $R_7$ or $R_8$ is a group of the formula (II).

Additionally preferred are photopolymerizable compositions where in the photoinitiator compounds of the formula (I)
X is S, a direct bond or $CR_{16}R_{17}$;
Y is O or S;
$R_1$, $R_3$, $R_4$, $R_5$, $R_6$ and $R_8$ are hydrogen;
$R_2$ and $R_7$ are a group of the formula (II) or (III);
$R_9$ and $R_{10}$ are $C_1$-$C_4$alkyl, in particular methyl;
$R_{11}$ is hydrogen;
$R_{12}$ and $R_{13}$ are $C_1$-$C_4$alkyl, in particular methyl;
$R_{14}$ and $R_{15}$ are $C_1$-$C_4$alkyl, in particular methyl; and
$R_{16}$ and $R_{17}$ are hydrogen or $C_1$-$C_8$alkyl, in particular methyl.

Further interesting are photopolymerizable compositions where in the photoinitiator compounds of the formula (I")
X is S, a direct bond or $CR_{16}R_{17}$;
Y is O or S;
$R_1$, $R_3$, $R_4$, $R_5$, $R_6$ and $R_8$ are hydrogen;
$R_2$ and $R_7$ are a group of the formula (II);
$R_9$ and $R_{10}$ are $C_1$-$C_4$alkyl, in particular methyl;
$R_{11}$ is hydrogen;
$R_{12}$ and $R_{13}$ are $C_1$-$C_4$alkyl, in particular methyl;
$R_{14}$ and $R_{15}$ are $C_1$-$C_4$alkyl, in particular methyl; and
$R_{16}$ and $R_{17}$ are hydrogen or $C_1$-$C_8$alkyl, in particular methyl.

Specifically excluded from the claims of the present invention are the compounds

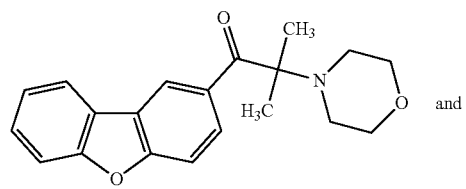

and

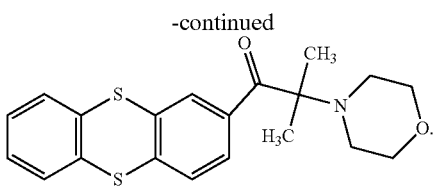

X is O, S, a direct bond or $CR_{16}R_{17}$.

Or X for example is S, a direct bond or $CR_{16}R_{17}$.

Y is O or S, in particular O.

$R_1$, $R_2$, $R_3$, $R_4$, $R_5$, $R_6$, $R_7$ and $R_8$ independently of each other for example are hydrogen, halogen, $C_1$-$C_4$alkyl, phenyl, $C_1$-$C_4$alkoxy, phenoxy, $C_1$-$C_4$alkylthio, phenylthio, di($C_1$-$C_4$alkyl)amino, N-morpholinyl, N-piperidinyl or a group of formula (II) or (III) as defined above.

Or $R_1$, $R_2$, $R_3$, $R_4$, $R_5$, $R_6$, $R_7$ and $R_8$ independently of each other for example are hydrogen, halogen, $C_1$-$C_4$alkyl, phenyl, $C_1$-$C_4$alkoxy, $C_1$-$C_4$alkylthio, di($C_1$-$C_4$alkyl)amino, N-morpholinyl, N-piperidinyl or a group of formula (II) or (III) as defined above.

Or $R_1$, $R_2$, $R_3$, $R_4$, $R_5$, $R_6$, $R_7$ and $R_8$ independently of each other for example are hydrogen, $C_1$-$C_4$alkyl, phenyl, $C_1$-$C_4$alkoxy or a group of formula (II) or (III) as defined above.

In particular $R_1$, $R_3$, $R_4$, $R_5$, $R_7$, $R_8$ are hydrogen and $R_2$ and $R_6$ are a group of formula (II) or (III).

$R_9$ and $R_{10}$ for example independently of each other are $C_1$-$C_4$alkyl or together with the C atom to which they are attached form a 5-membered or 6-membered carbocyclic ring.

Or $R_9$ and $R_{10}$ for example independently of each other are $C_1$-$C_4$alkyl or together with the C atom to which they are attached form a 6-membered or 7-membered carbocyclic ring.

Or $R_9$ and $R_{10}$ for example independently of each other are $C_1$-$C_4$alkyl, in particular methyl, or together with the C atom to which they are attached form a 6-membered carbocyclic ring (=a cyclohexyl ring).

$R_{11}$ is for example hydrogen, $C_1$-$C_4$alkyl, $C_5$-$C_7$cycloalkyl or Si($C_1$-$C_4$alkyl)$_3$.

Or $R_{11}$ is hydrogen, $C_1$-$C_4$alkyl, $C_5$-$C_7$cycloalkyl or 2-tetrahydropyranyl.

Or $R_{11}$ is hydrogen, $C_1$-$C_4$alkyl or $C_5$-$C_7$cycloalkyl, in particular hydrogen or $C_1$-$C_4$alkyl.

Preferably $R_{11}$ is hydrogen.

$R_{12}$ and $R_{13}$ independently of each other are $C_1$-$C_4$alkyl, unsubstituted phenyl-$C_1$-$C_4$alkyl, phenyl-$C_1$-$C_4$alkyl which is substituted by $C_1$-$C_4$alkyl or together with the C atom to which they are attached form a 5-membered, 6-membered or 7-membered carbocyclic ring.

Or $R_{12}$ and $R_{13}$ independently of each other are $C_1$-$C_4$alkyl, unsubstituted benzyl, methylbenzyl or together with the C atom to which they are attached form a 6-membered carbocyclic ring.

Or $R_{12}$ and $R_{13}$ independently of each other are $C_1$-$C_4$alkyl, benzyl or 4-methylbenzyl, in particular alkyl.

$R_{14}$ and $R_{15}$ independently of each other are $C_1$-$C_4$alkyl, $C_5$-$C_7$cycloalkyl, or together with the N atom to which they are attached form a 5-membered, 6-membered or 7-membered ring, which may contain additional heteroatoms O, S or N;

Or $R_{14}$ and $R_{15}$ independently of each other are $C_1$-$C_4$alkyl, or together with the N atom to which they are attached form a 5-membered or 6-membered ring, which may contain additional heteroatoms O or N.

Or $R_{14}$ and $R_{15}$ independently of each other are $C_1$-$C_4$alkyl, in particular methyl, or together with the N atom to which they are attached form a 5-membered or 6-membered ring, which may contain additional heteroatoms O or N.

Or $R_{14}$ and $R_{15}$ independently of each other are $C_1$-$C_4$alkyl, in particular methyl, or together with the N atom to which they are attached form morpholino or piperazino, in particular a morpholino ring.

$R_{16}$ and $R_{17}$ independently of each other are hydrogen, $C_1$-$C_8$alkyl, $C_5$-$C_7$cycloalkyl, benzyl, phenyl or together with the C atom to which they are attached form a 5 to 7 membered ring.

Or $R_{16}$ and $R_{17}$ independently of each other are hydrogen, $C_1$-$C_8$alkyl, or together with the C atom to which they are attached form a 5-membered, 6-membered or 7 membered ring, in particular a 5-membered or 6-membered ring.

Or $R_{16}$ and $R_{17}$ independently of each other are hydrogen or $C_1$-$C_8$alkyl, in particular methyl.

In accordance with the invention, the compounds of the formula (I) and (I'') can be used as photoinitiators for the photopolymerization of ethylenically unsaturated compounds.

The invention therefore also relates to photopolymerizable compositions comprising (A) at least one ethylenically unsaturated photopolymerizable compound and (B) at least one photoinitiator of the formula (I'') as defined above.

The composition may comprise additionally to the component (B), (x) at least one further photoinitiator (C), and/or (xi) further coinitiators (D) and/or (xii) other additives (D).

The unsaturated compounds may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Interesting also are resins which are modified with silicon or fluor, e.g. silicon acrylates. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, acrylated polyesters, polyesters containing vinyl ether or epoxy groups, and also acrylated polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the abovementioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof. Also suitable as components (A) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy) ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, 1-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Binders as well can be added to these novel compositions, and this is particularly expedient when the photopolymerizable compounds are liquid or viscous substances.

The quantity of binder may, for example, be 5-95%, preferably 10-90% and especially 40-90%, by weight relative to the overall solids content. The choice of binder is made depending on the field of application and on properties required for this field, such as the capacity for development in aqueous and organic solvent systems, adhesion to substrates and sensitivity to oxygen.

Examples of binders with high molecular weight (oligomeric) polyunsaturated compounds are acrylate epoxy resins, acrylate or vinyl-ether- or epoxy-group-containing polyesters, polyurethanes and polyethers.

Examples of suitable binders are polymers having a molecular weight of about 1000 to 2000000, preferably 10000 to 1000000. Examples are: homo- and copolymers of acrylates and methacrylates, for example copolymers of methyl methacrylate/ethyl acrylate/methacrylic acid, poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), and polyesters such as poly(ethylene glycol terephtalate) and poly(hexamethylene glycol succinate) and polyimides.

Suitable binders can also be a powder.

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment. The binder can simultaneously bear the radically photopolymerizable and the chemically or thermally curable function, providing a so-called dual-cure binder.

In addition to the photoinitiator the photopolymerizable mixtures may include various additives (D). Examples of these are thermal inhibitors, which are intended to prevent premature polymerization, examples being hydroquinone, hydroquinine derivatives, p-methoxyphenol, 1-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer.

Light stabilizers which can be added in a small quantity are UV absorbers, for example those of the hydroxyphenyl-benzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are disclosed in WO 04/074328, page 12, line 9 to page 14, line 23, said disclosure hereby is incorporated by reference.

Further additives known in the art may be added, as for example antistatics, flow improvers and adhesion promoters.

To accelerate the photopolymerization it is possible to add amines, for example triethanolamine, N-methyldiethanolamine, p-dimethylaminobenzoate or Michler's ketone.

The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention. Examples are mercaptanes, amines and benzothiazol.

Photopolymerization can also be accelerated by adding further photosentisizers which shift or broaden the spectral sensitivity. These are, in particular, aromatic carbonyl compounds, for example benzophenone, thioxanthone, anthraquinone and 3-acyl-coumarin derivatives, and also 3-(aroylmethylene)thiazolines, camphor quinone, but also eosine, rhodamine and erythrosine dyes, as well as all compounds which can be used as coinitiators as described above.

Examples of suitable sensitizer compounds (D) are disclosed in WO 06/008251, page 36, line 30 to page 38, line 8, the disclosure of which is hereby incorporated by reference.

The curing process can be assisted by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (D) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP 445624.

Further customary additives, depending on the intended use, are optical brighteners, fillers, pigments, dyes, wetting agents or levelling assistants.

In order to cure thick and pigmented coatings it is appropriate to add glass microspheres or pulverized glass fibres, as described for example in U.S. Pat. No. 5,013,768.

The compositions may also comprise dyes and/or white and colored pigments. Depending on the kind of application organic as well as anorganic pigments are used.

Such additives are known to the person skilled in the art, some examples are titan dioxide pigments, e.g. of the rutile type or anatas type, carbon black Russ, zinc oxide, such as zink white, iron oxide, such as iron oxide yellow, iron oxide red, chromium yellow, chromium green, nickel titanium yellow, ultramarine blue, cobalt blue, bismuth vanadate, cadmiumyellow or cadmium red. Examples of organic pigments are mono- or bisazo pigments, as well as metal complexes thereof, phthalocyanine pigments, polycyclic pigments, such as perylene-, anthraquinone-, thioindigo-, chinacridone- or triphenylmethane pigments, as well as diketo-pyrrolo-pyrole-, isoindolinone-, e.g. tetra-chlorisoindolinone-, isoindoline-, dioxazin-, benzimidazolone- and chinophthalone pigments.

The pigments are employed alone or in combination in the compositions according to the invention.

Depending on the intended use the pigments are used in amount customary in the art, for example in an amount of 1-60% by weight, or 10-30% by weight, based on the whole formulation.

The compositions may also comprise organic dyes of different classes. Examples are azo dyes, methin dyes, anthraquinone dyes or metal complex dyes. Customary concentrations are for example 0.1-20%, in particular 1-5%, based on the whole formulation.

The choice of additive is made depending on the field of application and on properties required for this field. The additives described above are customary in the art and accordingly are added in amounts which are usual in the respective application.

The invention also provides compositions comprising as component (A) at least one ethylenically unsaturated photopolymerizable compound which contains some solvent, is emulsified, dispersed or dissolved in water. Many variants of such radiation-curable aqueous prepolymer dispersions are commercially available.

A prepolymer dispersion is understood as being a dispersion of water and at least one prepolymer dispersed therein. The amount of radiation curable prepolymer or prepolymer mixture, dispersed in the water for example ranges from 20 to 95% by weight, in particular from 30 to 70% by weight. In these compositions the sum of the percentages given for water and prepolymer is in each case 100, with auxiliaries and additives (e.g. emulsifiers) being added in varying quantities depending on the intended use.

The radiation-curable aqueous prepolymer dispersions are known polymeric systems, comprising mono- or polyfunctional ethylenically unsaturated prepolymers, that have an average molecular weight $M_n$ (in g/mol) of at least 400, in particular from 500 to 100,000. Prepolymers with higher molecular weights, however, may also be considered depending on the intended application. Use is made, for example, of polyesters having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight $M_n$ (in g/mol) of at least 600, additionally comprising polymerizable C—C double bonds. Other suitable aqueous dispersions, based on specific alkyl (meth)acrylate polymers, are described in EP 41125.

Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel photoinitiators. It is of course also possible to use mixtures with known photoinitiators (C), for example mixtures with camphor quinone; benzophenone, benzophenone derivatives, such as 2,4,6-trimethylbenzophenone, 2-methyl benzophenone, 3-methylbenzophenone, 4-methyl benzophenone, 2-methoxycarbonylbenzophenone 4,4'-bis(chloromethyl)benzophenone, 4-chlorobenzophenone, 4-phenylbenzophenone, 3,3'-dimethyl-4-methoxybenzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone,

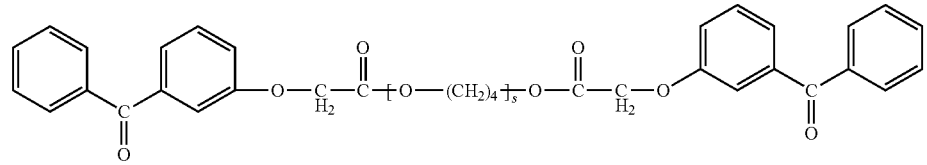

with s=1-20, a mixture of

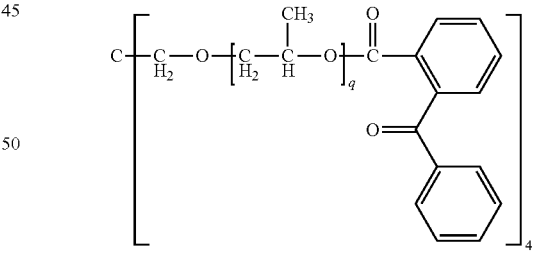

with q=about 2 and

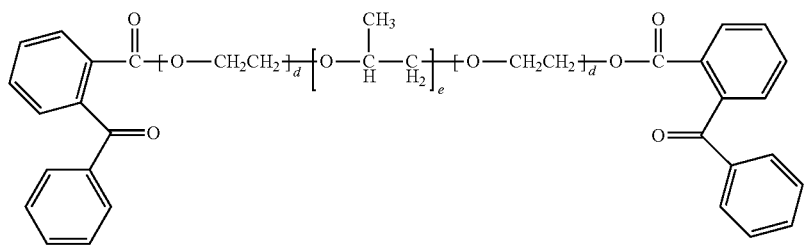

wherein the sum of d and e is about 14, where d is greater than e,

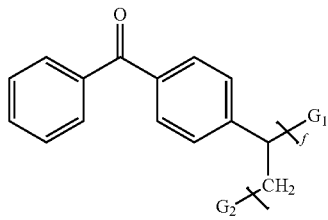

with f=about 14;

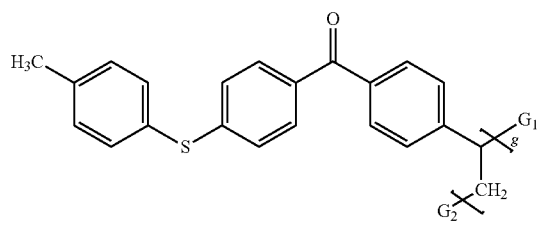

with g=about 12;

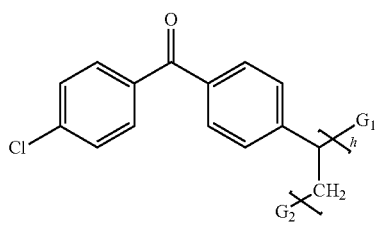

with h=about 13, and any blends or admixtures of the above mentioned compounds; thioxanthones, thioxanthone derivatives, polymeric thioxanthones as for example OMNIPOL TX; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropyl-benzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)-phenoxy]-phenyl}-2-methyl-propan-1-one; dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl)aminobenzoyl)-1-benzyl-1-dimethylaminopropane), (3,4-dimethoxybenzoyl)-1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenylacetoxy)-propoxy]-ethyl ester; ketosulfones, e.g. ESA-CURE KIP 1001 M; oximeesters, e.g. 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), peresters, e.g. benzophenone tetracarboxylic peresters as described for example in EP 126541, monoacyl phosphine oxides, e.g. (2,4,6-trimethyl-benzoyl)diphenylphosphine oxide, ethyl (2,4,6 trimethyl-benzoyl phenyl) phosphinic acid ester; bisacylphosphine oxides, e.g. bis(2,6-dimethoxy-benzoyl)-(2,4,4-trimethyl-pentyl)phosphine oxide, bis(2,4,6-trimethylbenzoyl)-phenylphosphine oxide, bis-(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaaryl-bisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl) titanium. Further, borate compounds can be used as coinitiators. As additional photoinitiators oligomeric compounds such as for example oligomeric alpha hydroxyl ketones e.g. 2-hydroxy-1-{1-[4-(2-hydroxy-2-methyl-propionyl)-phenyl]-1,3,3-trimethyl-indan-5-yl}-2-methyl-propan-1-one, ESACURE KIP, or oligomeric alpha amino ketones may be employed as well.

Where the novel photoinitiator systems are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17-25), aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene)($\eta^5$-cyclopentadienyl)iron (II) hexafluorophosphate or oxime sulfonates.

Suitable sulfonium salts are obtainable, for example, under the trade names Cyracure® UVI-6990, Cyracure® UVI-6974 (Union Carbide), Degacure® KI 85 (Degussa), SP-55, SP-150, SP-170 (Asahi Denka), GE UVE 1014 (General Electric), SarCat®KI-85 (=triarylsulfonium hexafluorophosphate; Sartomer), SarCat® CD 1010 (=mixed triarylsulfonium hexafluoroantimonate; Sartomer); SarCat® CD 1011(=mixed triarylsulfonium hexafluorophosphate; Sartomer).

Suitable iodonium salts are e.g. tolylcumyliodonium tetrakis(pentafluorophenyl)borate, 4-[(2-hydroxy-tetradecyloxy)phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate, 4-octyloxyphenyl-phenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxy-phenyliodonium hexafluorophosphate. Of all the iodonium salts mentioned, compounds with other anions are, of course, also suitable.

Suitable examples of oximesulfonates are α-(octylsulfonyloxyimino)-4-methoxybenzylcyanide, 2-methyl-α-[5-[4-

[[methyl-sulfonyl]oxy]imino]-2(5H)-thienylidene]-benzeneacetonitrile, 2-methyl-α-[5-[4-[[(n-propyl)sulfonyl]oxy]imino]-2(5H)-thienylidene]-benzeneacetonitrile, 2-methyl-α-[5-[4-[[(camphoryl)sulfonyl]oxy]imino]-2(5H)-thienylidene]-benzeneacetonitrile, 2-methyl-α-[5-[4-[[(4-methylphenyl)sulfonyl]oxy]imino]-2(5H)-thienylidene]-benzeneacetonitrile, 2-methyl-α-[5-[4-[[(n-octyl)sulfonyl]oxy]imino]-2(5H)-thienylidene]-benzeneacetonitrile, 2-methyl-α-[5-[[[[4-[[(4-methylphenyl)sulfonyl]oxy]phenyl]-sulfonyl]oxy]imino]-2(5H)-thienylidene]-benzeneacetonitrile, 1,1'-[1,3-propanediylbis(oxy-4,1-phenylene)]bis[2,2,2-trifluoro-bis[O-(trifluoromethylsulfonyl)oxime]-ethanone, 1,1'-[1,3-propanediylbis(oxy-4,1-phenylene)]bis[2,2,2-trifluoro-bis[O-(propylsulfonyl)oxime]-ethanone, 1,1'-[1,3-propanediylbis(oxy-4,1-phenylene)]bis[2,2,2-trifluoro-bis[O-((4-methylphenyl)sulfonyl)oxime]-ethanone, 2-[2,2,3,3,4,4,5,5,6,6,7,7-dodecafluoro-1-(nonafluorobutylsulfonyloxyimino)-heptyl]-fluorene, 2-[2,2,3,3,4,4,4-heptafluoro-1-(nonafluorobutylsulfonyloxyimino)-butyl]-fluorene, 2-[2,2,3,3,4,4,5,5,6,6,7,7-dodecafluoro-1-(nonafluorobutylsulfonyloxyimino)-heptyl]-9-thia-fluorene.

This list is not meant to be conclusive for additional photoinitiator compounds to be used in combination with the novel compounds of the inventions.

The photopolymerizable compositions generally comprise 0.05 to 15% by weight, preferably 0.1 to 10% by weight, of the photoinitiator, based on the composition. The amount refers to the sum of all photoinitiators added, if mixtures of initiators are employed. Accordingly, the amount either refers to the photoinitiator (B) or the photoinitiators (B)+(C).

The photopolymerizable compositions can be used for various purposes, for example printing, such as intaglio printing, flexographic printing, screen printing, offset printing, gravure printing, lithography or continuous or dropwise ink-jet printing on for example material pretreated in accordance with the process as disclosed in WO 03/064061 using generally known formulations, for example in publishing, packaging or shipping, in logistics, in advertising, in security printing or in the field of office equipment, as a clear finish, as a colored finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as photoresists, e.g. etch resists, electroplating resists, or permanent resists, both liquid and dry films, as photostructurable dielectricum and as solder masks for electronic circuits, as resists to manufacture color filters for any type of display applications or to generate structures in the manufacturing process of plasma-display panels and electroluminescence displays, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres, or for producing optical lenses, e.g. contact lenses or Fresnel lenses.

The compositions according to the invention are further suitable for the production of medical equipment, auxiliaries or implants.

Further the compositions according to the invention are suitable for the preparation of gels with thermotropic properties, as for example described in DE 19700064 and EP 678534.

The compositions according to the invention can also be used in dry paint film, as for example described in Paint & Coatings Industry, April 1997, 72 or Plastics World, vol. 54, no. 7, p 48(5).

The novel photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions act as a crosslinking agent which renders the film insoluble. The monounsaturated monomer functions act as a reactive diluent, which is used to reduce the viscosity without the need to employ a solvent.

Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiators and photoinitiator mixtures can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics.

In addition to the novel photoinitiators, the powder coating formulations may also include UV absorbers. To appropriate examples is referred above.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating techniques, for example by printing, e.g. by intaglio printing, lithographic printing, flexographic printing, inkjet printing, screen printing, gravure printing, spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.01 μm to more than 100 μm, for example 20 mm or 0.02 to 10 cm, preferably 0.5 to 100 μm.

The compositions according to the invention are also suitable for use in uv-curing adhesives, e.g. in the preparation of pressure-sensitive adhesives, laminating adhesives, hot-melt adhesives, moisture-cure adhesives, silane reactive adhesives or silane reactive sealants and the like, and related applications.

Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The novel photoinitiators further find application in formulations for negative resists, having a very high sensitivity to light and being able to be developed in an aqueous alkaline medium without swelling. They are suitable as photoresists for electronics (electroplating resist, etch resist, solder resist), the production of printing plates, such as offset printing plates or flexo printing plates, for the production of printing forms for relief printing, planographic printing, rotogravure or of screen printing forms, for the production of relief copies, for example for the production of texts in braille, for the production of stamps, for use in chemical milling or as a microresist in the production of integrated circuits. The possible layer supports, and the processing conditions of the coating substrates, are just as varied.

The compositions according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 μm to 10 μm, while for printed circuits it is from 1.0 μm to about 100 μm.

Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.-P. Nicolay in Offset Printing 1997, 6, p. 34-37.

Following the imagewise exposure of the material and prior to development, it may be advantageous to carry out thermal treatment for a short time. In this case only the exposed sections are thermally cured. The temperatures employed are generally 50-150° C., preferably 80-130° C.; the period of thermal treatment is in general between 0.25 and 10 minutes.

Conjugated polymers, like e.g. polyanilines can be converted from a semiconductive to a conductive state by means of proton doping. The oxime-sulfonates of the present invention can also be used to imagewise irradiate compositions comprising such conjugated polymers in order to form conducting structures (exposed areas) embedded in insulating material (non-exposed areas). Such materials can for example be used as wiring and connecting parts for the production of electric and electronic devices.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset and flexo inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Another field where photocuring is employed is the coating of metals, in the case, for example, of the coating of metal plates and tubes, cans or bottle caps, and the photocuring of polymer coatings, for example of floor or wall coverings based on PVC.

Examples of the photocuring of paper coatings are the colourless varnishing of labels, record sleeves and book covers.

Also of interest is the use of the novel compounds and photoinitiator systems for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366-370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing usually is carried out using medium-pressure mercury lamps as are conventional in UV curing. However, there is also particular interest in less intense lamps, for example of the type TL 40 W/03 or TL40 W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists.

The photopolymerizable compositions further can be used for the production of functional glass, as is for example described in JP 10 287450 A.

The photocurable compositions of the invention can further be used for curing of charged monomers, e.g. acrylates with $NH_4Cl$-groups etc. usw. Such compositions are for example employed for preparing polyelektrolytes or corresponding copolymers.

The invention also provides a process for the photopolymerization of monomeric, oligomeric or polymeric compounds containing at least one ethylenically unsaturated double bond, which comprises adding to the abovementioned compounds at least one photoinitiator compound of the formula (I) or at least one photoinitiator compound of the formula (I″) as described above and irradiating the resulting composition with electromagnetic radiation, for example light of the wavelength 200 to 600 nm or with particulate radiation, such as for example electron beam or X-ray; as well as the use of a photoinitiator or photoinitiator mixture as defined above for the photopolymerization of monomeric, oligomeric or polymeric compounds containing at least one ethylenically unsaturated double bond.

Subject of the invention also is a process as described above for the preparation of pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

The invention further provides a coated substrate which is coated on at least one surface with a composition as described above, and a polymerized or crosslinked composition obtained by curing a polymerizable composition as described above.

The sensitivity of the novel compositions to radiation generally extends from about 190 nm through the UV region and into the infrared region (about 20,000 nm, in particular 1200 nm), especially from 190 nm to 650 nm (depending on the photoinititator moiety, optionally in combination with a sensitizer as described hereinbefore) and therefore spans a very broad range. Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, super high-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, electron beams and X-rays. The distance between the lamp and the substrate to be exposed in accordance with the invention may vary depending on the intended application and the type and output of lamp, and may be, for example, from 1 cm to 150 cm. Laser light sources, for example excimer lasers, such as krypton F lasers for exposure at 248 nm are also suitable. Lasers in the visible region can also be employed.

Alternatively, the actinic radiation is provided by light emitting diodes (LED) or organic light emitting diodes (OLED), e.g. UV light emitting diodes (UV-LED). Said LEDs allow instant on and off switching of the radiation source. Further, UV-LEDs generally have a narrow wavelength distribution and offer the possibility to customize the peak wavelength and also provide an efficient conversion of electric energy to UV radiation.

As mentioned above, depending on the light source used it is advantageous in many cases to employ a sensitizer, as described above, whose absorption spectrum coincides as closely as possible to the emission spectrum of the radiation source. The examples which follow illustrate the invention in more detail, without restricting the scope said examples only. Parts and percentages are, as in the remainder of the description and in the claims, by weight, unless stated otherwise. Where alkyl radicals having more than three carbon atoms are referred to in the examples without any mention of specific isomers, the n-isomers are meant in each case.

SYNTHESIS EXAMPLES

Example 1: 2-Hydroxy-1-[7-(2-hydroxy-2-methyl-propanoyl)-9H-xanthen-2-yl]-2-methyl-propan-1-one (Cmpd 1)

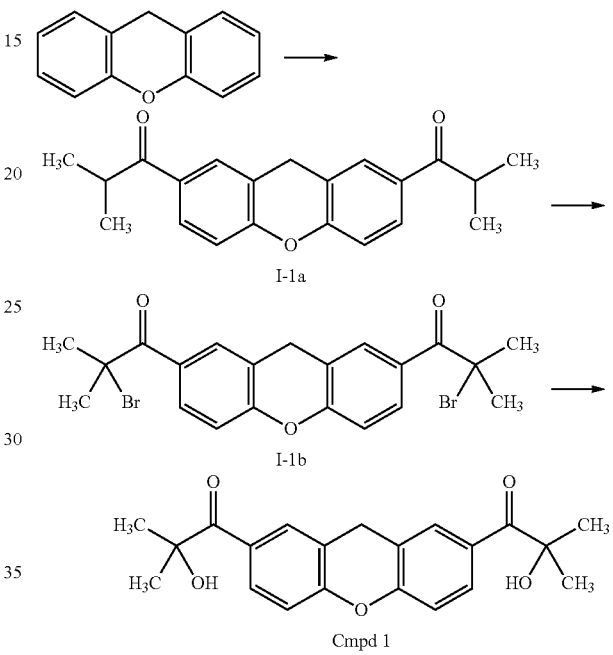

Intermediate I-1a: 2-methyl-1-[7-(2-methylpropanoyl)-9H-xanthen-2-yl]propan-1-one Isobutyroyl chloride (26.64 g, 0.25 mol) and xanthene (18.22 g, 0.1 mol) are dissolved in 100 ml of 1,2-dichloroethane and the solution is cooled to −15° C. To the stirred solution is then added aluminium trichloride (33.3 g, 0.25 mol) within 30 minutes and a temperature between −10 to −15° C. The resulting orange mixture is then stirred 18 h at room temperature and is thereafter slowly poured in a stirred mixture of 600 g of ice, 50 ml of 32% hydrochloric acid and 150 ml of dichloromethane. The organic layer is separated, washed with 50 ml of 5% HCl, 1 M $Na_2CO_3$ and water, dried over $MgSO_4$ and evaporated. The residue is recrystallized from dichloromethane-methanol to afford 29.2 g of the title compound as a white solid, mp. 125-131° C.

$^1$H-NMR ($CDCl_3$, 400 MHz, δ ppm): 7.83-7.81 (m, 4ArH), 7.10-7.07 (m, 2 ArH), 4.13 (s, 2H, $CH_2$), 3.55-3.49 (m, 2H), 1.21 (d, 12H).

Intermediate I-1b: 2-bromo-1-[7-(2-bromo-2-methyl-propanoyl)-9H-xanthen-2-yl]-2-methyl-propan-1-one Intermediate I-1a (24.18 g, 0.075 mol) is dissolved in 100 ml of dichloromethane and the solution is cooled to 3° C. To the stirred solution is then added the solution of bromine (24.0 g, 0.15 mol) in 75 ml of dichloromethane at a temperature between 3 to 5° C. within 1 h. The mixture is then stirred for 3 h at room temperature and then diluted with 200 ml of cold water. The organic layer is separated, washed with 100 ml 1 M NaHCO$_3$ and water, dried over MgSO$_4$ and evaporated. The residue is recrystallized from dichloromethane-acetonitrile to afford 26.5 g of the title compound as a white solid, mp. 129-138° C.

$^1$H-NMR (CDCl$_3$, 400 MHz, δ ppm): 8.15-8.10 (m, 4ArH), 7.10-7.08 (m, 2 ArH), 4.16 (s, 2H, CH$_2$), 2.08 (s, 12H).

Cmpd. 1:

Intermediate I-1b (8.64 g, 0.018 mol) is dissolved in 35 ml of tetrahydrofurane. To this solution is then added the solution of NaOH (2.88 g, 0.072 mol) in 14 ml of water. The resulting emulsion is vigorously stirred for 26 h at room temperature. Thereafter dichloromethane (60 ml), water (100 ml) and 1M HCl (40 ml) is added. The organic layer is separated, washed with water, dried over MgSO$_4$ and evaporated. The residue is recrystallized from ethylacetate to afford 5.1 g of the title compound as a white solid, mp. 159-162° C.

$^1$H-NMR (CDCl$_3$, 400 MHz, δ ppm): 7.98-7.94 (m, 4ArH), 7.11-7.08 (m, 2 ArH), 4.14 (s, 2H, CH$_2$), 4.04 (s, 20H), 1.63 (s, 12H).

Example 2: 2-Hydroxy-1-[7-(2-hydroxy-2-methyl-propanoyl)-9,9-dimethyl-xanthen-2-yl]-2-methyl-propan-1-one (Cmpd 2)

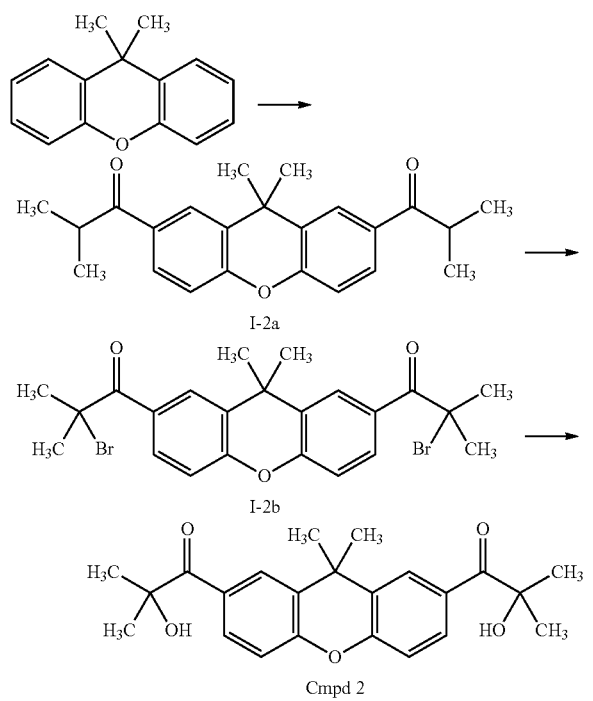

Cmpd 2

Intermediate I-2a: 1-[9,9-dimethyl-7-(2-methylpropanoyl)xanthen-2-yl]-2-methyl-propan-1-one The intermediate I-2a is prepared from 9,9-dimethylxanthene in analogy to intermediate I-1a in 85% yield. White solid, mp. 105-109° C.

$^1$H-NMR (CDCl$_3$, 400 MHz, δ ppm): 8.15-8.14 (d, 2 ArH), 7.88-7.85 (dd, 2 ArH), 7.15-7.13 (d, 2 ArH), 3.61-3.54 (m, 2H), 1.72 (s, 2×CH$_3$) 1.26-1.24 (d, 12H).

Intermediate I-2b: 2-bromo-1-[7-(2-bromo-2-methyl-propanoyl)-9,9-dimethyl-xanthen-2-yl]-2-methyl-propan-1-one The intermediate I-2b is prepared from intermediate I-2a in analogy to intermediate I-1b in 89.3% yield. White solid, mp. 118-130° C.

$^1$H-NMR (CDCl$_3$, 400 MHz, δ ppm): 8.38-8.37 (d, 2ArH), 8.19-8.16 (dd, 2 ArH), 7.14-7.11 (d, 2 ArH), 2.08 (s, 12H), 1.73 (s, 2×CH$_3$).

Cmpd. 2:

Cmpd 2 is prepared from intermediate I-2b in analogy to Cpmd. 1 in 93.2% yield. White solid, mp. 107-119° C.

$^1$H-NMR (CDCl$_3$, 400 MHz, δ ppm): 8.27-8.26 (d, 2 ArH), 8.01-7.99 (dd, 2 ArH), 7.14-7.12 (d, 2 ArH), 4.09 (bs, 2×OH), 1.72 (s, 2×CH$_3$), 1.66 (s, 12H).

Example 3: 2-Hydroxy-1-[8-(2-hydroxy-2-methyl-propanoyl)phenoxathiin-2-yl]-2-methyl-propan-1-one (Cmpd 3)

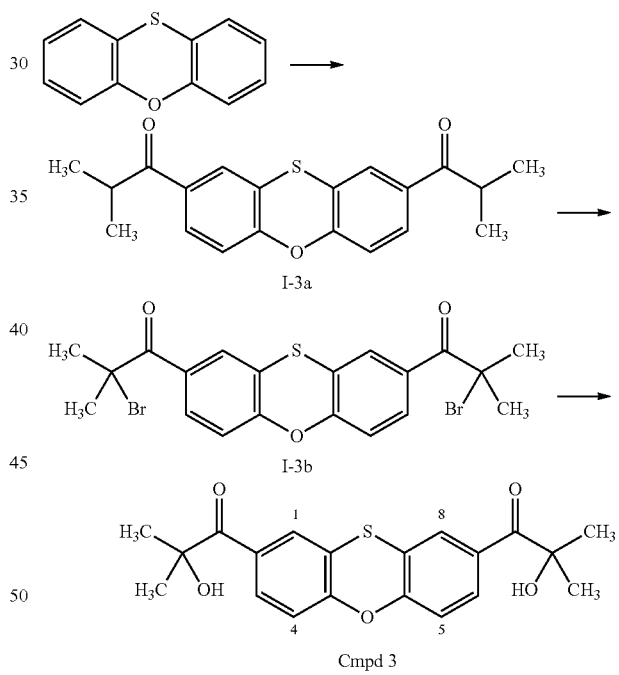

Cmpd 3

Intermediate I-3a: 2-methyl-1-[8-(2-methylpropanoyl)phenoxathiin-2-yl]propan-1-one The intermediate I-3a is prepared from phenoxantiin in analogy to intermediate I-1a in 77% yield (after two crystallizations from methanol). Light yellow solid, mp. 82-92° C. According to NMR it consists of two regioisomers in ca 1:1 ratio. The isobutyroyl groups in these regioisomers are presumably in positions 2,7 respectively 2,8 of the phenoxanthiin ring system.

$^1$H-NMR (CDCl$_3$, 400 MHz, δ ppm): 7.74-6.98 (m, 6 ArH), 3.48-3.41 (m, 2H), 1.27-1.17 (m, 12H).

Intermediate I-3b: 2-bromo-1-[8-(2-bromo-2-methyl-propanoyl)phenoxathiin-2-yl]-2-methyl-propan-1-one The intermediate I-3b is prepared from intermediate I-3a in analogy to intermediate I-1b in 91.5% yield. Yellow solid, mp. 104-131° C. According to NMR it consists of two regiosomers in ca 1:1 ratio. The isobutyroyl groups in these regioisomers are presumably in positions 2,7 respectively 2,8 of the phenoxanthiin ring system.

$^1$H-NMR (CDCl$_3$, 400 MHz, δ ppm): 8.06-7.0 (m, 6 ArH), 2.04 (s, 6H), 2.03 (s, 6H)

Cmpd. 3:

Cmpd 3 is prepared from intermediate I-3b in analogy to Cpmd. 1, Table 1 in 78% yield. Yellow solid, mp. 119-125° C. According to NMR it consists of two regiosomers in ca 1:1 ratio. The isobutyroyl groups in these regioisomers are presumably in positions 2,7 respectively 2,8 of the phenoxanthiin ring system.

$^1$H-NMR (CDCl$_3$, 400 MHz, δ ppm): 7.89-7.0 (m, 6 ArH), 3.81 (s, OH), 3.79 (s, OH), 1.61 (s, 6H), 1.60 (s, 6H).

Example 4: 2-Hydroxy-1-[8-(2-hydroxy-2-methyl-propanoyl)thianthren-2-yl]-2-methyl-propan-1-one (Cmpd 4)

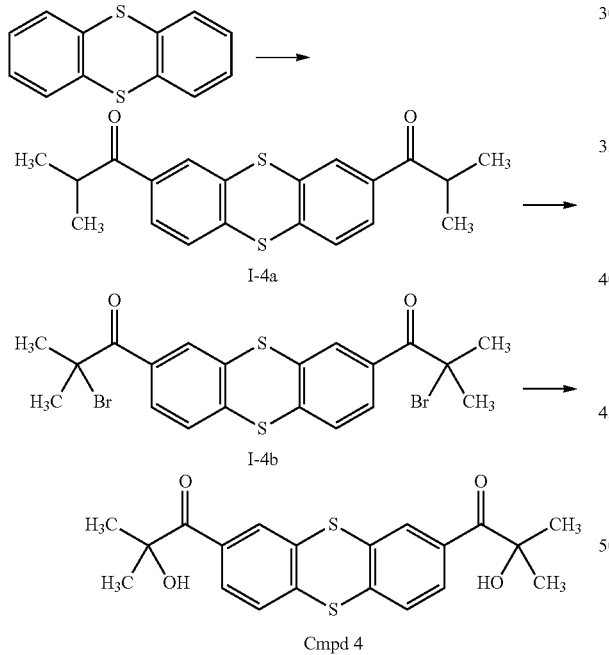

Intermediate I-4a: 2-methyl-1-[8-(2-methylpropanoyl)thianthren-2-yl]propan-1-one The intermediate I-4a is prepared from thianthren in analogy to intermediate I-1a in 24.5% yield (after two crystallizations from acetonitril). Light yellow solid, mp. 98-110° C.

$^1$H-NMR (CDCl$_3$, 400 MHz, δ ppm): 8.01-8.00 (d, 2 ArH), 7.83-7.80 (dd, 2 ArH), 7.54-7.52 (d, 2 ArH), 3.53-3.44 (m, 2 CH), 1.21-1.19 (d, 12H).

Intermediate I-4b: 2-bromo-1-[8-(2-bromo-2-methyl-propanoyl)thianthren-2-yl]-2-methyl-propan-1-one The intermediate I-4b is prepared from intermediate I-4a in analogy to intermediate I-1b in 95% yield. Yellow solid, mp. 114-118° C.

$^1$H-NMR (CDCl$_3$, 400 MHz, δ ppm): 8.22-8.21 (d, 2 ArH), 8.10-8.07 (dd, 2 ArH), 7.55-7.53 (d, 2 ArH), 2.03 (s, 12H).

Cmpd. 4:

Cmpd 4 is prepared from intermediate I-4b in analogy to Cpmd. 1 in 79% yield. Yellow solid, mp. 143-147° C.

$^1$H-NMR (CDCl$_3$, 400 MHz, δ ppm): 7.76-7.75 (d, 2 ArH), 7.59-7.56 (dd, 2 ArH), 7.06-7.04 (d, 2 ArH), 3.31 (s, OH), 1.10 (s, 12H).

Example 5: 2-Hydroxy-1-[8-(2-hydroxy-2-methyl-propanoyl)dibenzofuran-2-yl]-2-methyl-propan-1-one, (Cmpd 5)

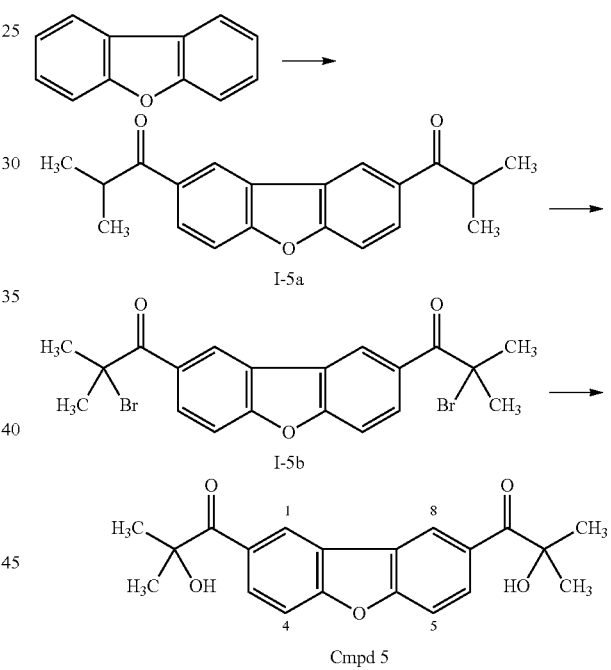

Intermediate I-5a: 2-methyl-1-[8-(2-methylpropanoyl)dibenzofuran-2-yl]propan-1-one The intermediate I-5a is prepared from dibenzofurane in analogy to intermediate I-1a. The crude product was obtained in 99% yield as a viscous, light yellow oil.

$^1$H-NMR (CDCl$_3$, 400 MHz, δ ppm): 8.65-8.64 (d, 2 ArH), 8.17-8.14 (dd, 2 ArH), 7.66-7.64 (d, 2 ArH), 3.71-3.63 (m, 2 CH), 1.29-1.27 (d, 12H).

Intermediate I-5b: 2-bromo-1-[8-(2-bromo-2-methyl-propanoyl)dibenzofuran-2-yl]-2-methyl-propan-1-one The intermediate I-5b is prepared from intermediate I-5a in analogy to intermediate I-1b in 69% yield (after crystallization from methanol). Off white solid, mp. 127-160° C., purity about 95% by $^1$H-NMR.

$^1$H-NMR (CDCl$_3$, 400 MHz, δ ppm): 8.89-8.88 (d, 2 ArH), 8.47-8.44 (dd, 2 ArH), 7.67-7.64 (d, 2 ArH), 2.14 (s, 12H).

Cmpd. 5:

Cmpd 5 is prepared from intermediate I-5b in analogy to Cpmd. 1 in 69.5% yield. White solid, mp. 121-148° C., purity about 95% by $^1$H-NMR.

$^1$H-NMR (CDCl$_3$, 400 MHz, δ ppm): 8.81-8.80 (d, 2 ArH), 8.30-8.28 (dd, 2 ArH), 7.68-7.66 (d, 2 ArH), 3.89 (bs, 2 OH), 1.74 (s, 12H).

Example 6: 2-(dimethylamino)-1-[8-[2-(dimethyl-amino)-2-methyl-propanoyl]phenoxathiin-2-yl]-2-methyl-propan-1-one (Cmpd 6)

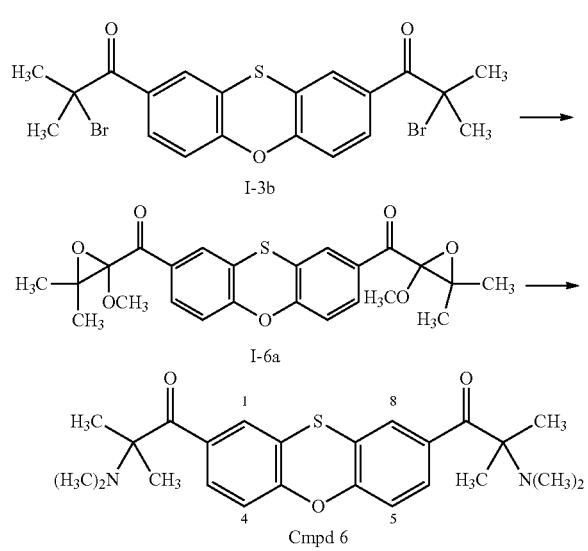

Intermediate I-6a: [8-(2-methoxy-3,3-dimethyl-oxi-rane-2-carbonyl)phenoxathiin-2-yl]-(2-methoxy-3,3-dimethyl-oxiran-2-yl)methanone To a stirred suspension of 2-bromo-1-[8-(2-bromo-2-methyl-propanoyl)phenoxathiin-2-yl]-2-methyl-propan-1-one (intermediate I-3b, 24.91 g, 0.05 mol) in 150 ml of methanol is added the solution of sodium methoxide (5.94 g, 0.11 mol in 45 ml of methanol at 0° C. within 30 minutes. The mixture is then stirred for 96 h at room temperature and the methanol is evaporated under reduced pressure. The residue is dissolved in 40 ml of water and 150 ml of dichloromethane, the organic layer is separated, washed with 50 ml of water, dried over MgSO$_4$ and evaporated to afford 20.8 g of the crude title compound as a thick yellow oil.

$^1$H-NMR (CDCl$_3$, 400 MHz, δ ppm): 7.28-7.01 (m, 6 ArH), 3.23-3.19 (bs, 2 OCH$_3$), 1.50 (bs, 2×CH$_3$), 1.04 (bs, 2×CH$_3$).

Cmpd. 6:

A 350 ml steel autoclave is charged with intermediate I-6a (20.35 g, ca 0.05 mol), 40 ml of xylene and dimethylamine (14.25 g of a 33% solution in ethanol, 0.104 mol). The autoclave is thereafter heated for 20 h at 130° C. and then cooled to room temperature.

The reaction mixture is evaporated and the oily residue is chromatographed on silica gel with ethyl acetate-heptane 1:6. The pure fraction is recrystallized twice from methanol to afford 9.22 g of the title compound as a light yellow solid, mp. 138-147° C. According to NMR it consists of two regioisomers in ca 1:1 ratio. The dimethylamino-isobutyroyl groups in these regioisomers are presumably in positions 2,7 respectively 2,8 of the phenoxanthiin ring system.

$^1$H-NMR (CDCl$_3$, 400 MHz, δ ppm): 8.34-8.16 (m, 4 ArH), 7.10-6.97 (m, 2 ArH), 2.26 (s, 6H, CH$_3$), 2.25 (s, 6H, CH$_3$), 1.28 (s, 6H, CH$_3$), 1.27 (s, 6H, CH$_3$).

Example 7: 2-(Dimethylamino)-1-[7-[2-(dimethyl-amino)-2-methyl-propanoyl]-9,9-dimethyl-xanthen-2-yl]-2-methyl-propan-1-one (Cmpd 7)

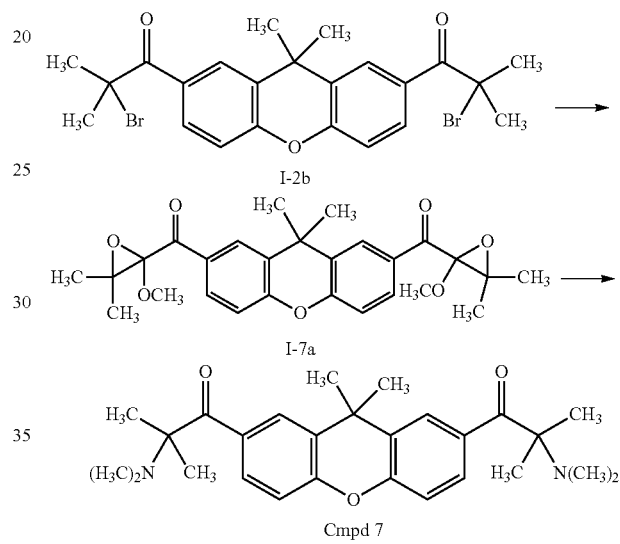

Intermediate I-7a: [7-(2-methoxy-3,3-dimethyl-oxi-rane-2-carbonyl)-9,9-dimethyl-xanthen-2-yl]-(2-methoxy-3,3-dimethyl-oxiran-2-yl)methanone The intermediate I-7a is prepared from intermediate I-2b in analogy to intermediate I-6a in ca 99% yield (crude) as a thick yellow oil.

$^1$H-NMR (CDCl$_3$, 400 MHz, δ ppm): 7.51-7.49 (bs, 2 ArH), 7.31-7.28 (dd, 2 ArH), 7.08-7.06 (d, 2 ArH), 3.21 (s, 2×OCH$_3$), 1.67 (bs, 2×CH$_3$), 1.56 (s, 2×CH$_3$), 1.03 (s, 2×CH$_3$).

Cmpd. 7:

Cmpd 7 is prepared from intermediate I-7a in analogy to Cpmd. 6, Table 1 in 8% yield. White solid, mp. 152-173° C., purity about 95% by $^1$H-NMR.

$^1$H-NMR (CDCl$_3$, 400 MHz, δ ppm): 8.72 (bs, 2 ArH), 7.52-7.50 (d, 2 ArH), 7.02-7.0 (d, 2 ArH), 2.28 (s 4×CH$_3$), 1.68 (s, 2×CH$_3$), 1.28 (s, 4×CH$_3$).

APPLICATION EXAMPLES

Example A1: Photocuring of a Radically Polymerizable Clear Coating Formulation

The compounds of the invention are evaluated in a clear coat formulation consisting of the following mixture:

20 wt. % of the polyester-acrylate Laromer@ PE 9079 (BASF) and 80 wt. % of the amine-modified polyether-acrylate Laromer@ PO 94F (BASF).

Unless mentioned otherwise, each compound is evaluated at a level of 4 wt. % in this liquid radically curable coating formulation. After proper dissolution (clear solution) of the photoinitiator compound, the formulation is applied by means of the draw-down technique at a wet film thickness of 12 μm onto a white cardboard (100×150 mm). The coated substrate is then placed on the conveyor belt of an IST-METZ GmbH photocuring equipment (model "M-30-2x1-BLKU-TR-5-SS-N2-SLR") fitted with air-cooled cold mirror reflectors (CMK) and with 1 medium pressure mercury lamp operated at 200 W/cm. The quality of the photocuring reaction under normal conditions, i.e. not under inert atmosphere), is assessed immediately after irradiation by means of the dry rub resistance (DRR) test: satisfactory curing is achieved when the coated surface is free from any trace after rubbing the surface with a paper tissue. The efficiency of the photoinitiator is quantified by the cure speed of the formulation, which is defined as the maximum belt speed (in m/min.) at which satisfactory cure (passed DRR test) is still achieved.

The results are summarized in Table 1. It is clearly seen that compounds of the present invention, e.g. compounds Nr. 2 and Nr. 5, exhibit significantly higher curing speed than the state of the art photoinitiator compounds, e.g. the monofunctional α-hydroxyketone (AHK) Irgacure® 184 (BASF) and Esacure®KIP 150 (Lamberti), as well as the difunctional AHK Esacure® One (Lamberti).

TABLE 1

| Compound (weight-%) | Curing speed (m/min) |
|---|---|
| Cmpd 2 (4) | 105 |
| Cmpd 5 (4) | 110 |
| Irgacure ® 184 (4) | 65 |
| Esacure ® KIP 150 (4) | 75 |
| Esacure ® One (4) | 85 |

Example A2: Photocuring of a Radically Polymerizable Blue Flexo Ink Formulation

The photoinitiator are evaluated in a the blue flexo ink formulation as detailed in Table 2.

TABLE 2

| Blue flexo ink formulation | | |
|---|---|---|
| wt % | ingredient | Product name |
| 14.0 | Polyester-acrylate | Laromer ® LR 8800 (BASF) |
| 12.0 | Polyester-acrylate | Ebecryl ® 450 (Allnex) |
| 24.0 | Polyether-acrylate | Laromer ® PO 94F (BASF) |
| 32.3 | Pentaerythritol tetraacrylate (PPT-TA, diluent) | Laromer ® PPTTA (BASF) |
| 1.0 | Dispersing agent | Efka ® PX 4701 (BASF) |
| 0.2 | Levelling agent | Efka ® 7305 (BASF) |
| 16.0 | Pigment | Heliogen ® Blue D7110F (BASF) |
| 0.5 | PE wax | Luwax ® AF 30 Mikropulver (BASF) |

Unless mentioned otherwise, each compound is evaluated at a level of 5 wt. % in the radically curable blue flexo ink formulation (i.e. 5 g of the photoinitiator compound+95 g of the formulation as described in Table 2). The ink is applied by means of a laboratory flexo ink applicator "Prüfbau" (Prüfbau Mehrzweck Probedruckmaschine Typ MZ-2) at a wet film thickness of 1.6 g/m² onto a freshly Corona treated white polyester (PE) film. The coated substrate is then placed on the conveyor belt of an IST-METZ GmbH photocuring equipment (model "M-30-2x1-BLKU-TR-5-SS-N2-SLR") fitted with air-cooled cold mirror reflectors (CMK) and with 1 medium pressure mercury lamp operated at 200 W/cm. The complete through-cure of the ink under normal conditions (i.e. not under inert atmosphere), is assessed immediately after irradiation by means of the REL test (DIN EN 20105-A02&A03): satisfactory curing is achieved when the coated surface is free from any trace after rubbing the surface with a paper tissue. The efficiency of the photoinitiator is quantified by the cure speed of the formulation, which is defined as the maximum belt speed (in m/min.) at which satisfactory cure (passed REL test) is still achieved.

The results are summarized in Table 3. It is clearly seen that compounds of the present invention exhibit higher curing speed than the state of the art photoinitiators for flexo inks, i.e. the α-aminoketones (AAK) 2-(4-methylbenzyl)-2-(dimethylamino)-1-[4-(4-morpholinyl)phenyl]-1-butanone (Irgacure® 379, BASF) and 2-methyl-1-[4-(methylthio)phenyl]-2-(4-morpholinyl)-1-propanone (Irgacure® 907, BASF), but also than the difunctional AHK 2-hydroxy-1-{4-[4-(2-hydroxy-2-methyl-propionyl)-benzyl]-phenyl}-2-methyl-propan-1-one (Irgacure® 127, BASF), used as reference materials.

TABLE 3

| Compound (weight-%) | Curing speed (m/min) |
|---|---|
| Cmpd 2 (5) | 110 |
| Irgacure ® 379 (5) | 80 |
| Irgacure ® 907 (5) | 70 |
| Irgacure ® 127 (5) | 55 |

Example A3: Photocuring of a Radically Polymerizable Yellow Flexo Ink Formulation Considering the high efficiency of the photoinitiator comp 2 in both the clear coating formulation and the blue flexo ink, it is also evaluated into the yellow flexo ink formulation detailed in Table 4.

TABLE 4

| Yellow flexo ink formulation | | |
|---|---|---|
| wt % | ingredient | Product name |
| 13.0 | Amine-modified polyether-acrylate | Laromer PO 94F (BASF) |
| 11.0 | Polyester-acrylate | Laromer PE 44F (BASF) |
| 36.0 | Amine-modified polyether-acrylate | Laromer LR 8996 (BASF) |
| 24.5 | Trimethylolpropane ethoxy triacrylate (TMPETOA, diluent) | Laromer LR 8863 (BASF) |
| 2.5 | Dispersing agent | Efka ® PX 4701 (BASF) |
| 0.2 | Levelling agent | Efka ® 7305 (BASF) |
| 12.4 | Pigment | Irgalite Yellow D1115/BAW (BASF) |
| 0.4 | PE wax | Luwax ® AF 30 Mikropulver (BASF) |

Each photoinitiator compound is evaluated at a level of 5 wt. % in the radically curable yellow flexo ink formulation (i.e. 5 g of PI+95 g of formulation in Table 5). The ink is applied by means of a laboratory flexo ink applicator "Prüfbau" (Prüfbau Mehrzweck Probedruckmaschine Typ MZ-2) at a wet film thickness of 1.6 g/m² onto a freshly Corona treated white PE film. The coated substrate is then placed on the conveyor belt of an IST-METZ GmbH photocuring equipment (model "M-30-2×1-BLKU-TR-5-SS-N2-SLR") fitted with air-cooled cold mirror reflectors (CMK) and with 1 medium pressure mercury lamp operated at 200 W/cm. The complete through-cure of the ink under normal conditions, i.e. not under inert atmosphere), is assessed immediately after irradiation by means of the REL test (DIN EN 20105-A02&A03): satisfactory curing is achieved when the coated surface is free from any trace after rubbing the surface with a paper tissue. The efficiency of the photoinitiator is quantified by the cure speed of the formulation, which is defined as the maximum belt speed (in m/min.) at which satisfactory cure (passed REL test) is still achieved.

The results are summarized in Table 5. It is clearly seen that compound Nr. 2 of the present invention exhibits significantly higher curing efficiency than the state of the art photoinitiator for flexo inks, i.e. the α-aminoketone 2-(4-methylbenzyl)-2-(dimethylamino)-1-[4-(4-morpholinyl)phenyl]-1-butanone (Irgacure® 379, BASF).

TABLE 5

| Compound (weight-%) | Curing speed (m/min) |
|---|---|
| Cmpd 2 (5) | 70 |
| Irgacure ® 379 (5) | 30 |

The invention claimed is:
1. A photopolymerizable composition comprising:
(A) at least one ethylenically unsaturated photopolymerizable compound and
(B) at least one photoinitiator compound of formula (I):

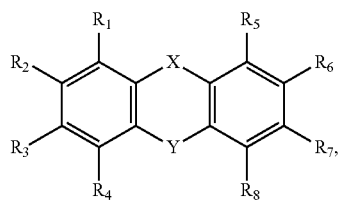

wherein
X is O, S, a direct bond or $CR_{16}R_{17}$;
Y is O or S;
$R_1$, $R_2$, $R_3$, $R_4$, $R_5$, $R_6$, $R_7$ and $R_8$ independently of each other are hydrogen, halogen, $C_1$-$C_4$alkyl, $C_5$-$C_7$cycloalkyl, phenyl, $C_1$-$C_4$alkoxy, $C_5$-$C_7$cycloalkoxy, phenoxy, $C_1$-$C_4$alkylthio, $C_5$-$C_7$cycloalkylthio, phenylthio, di($C_1$-$C_4$alkyl)amino, di($C_5$-$C_7$cycloalkyl)amino, N-morpholinyl, N-piperidinyl or a group of formula (II) or (III):

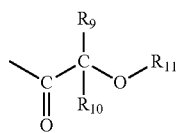

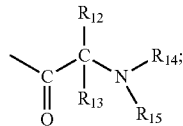

provided that
one of $R_1$, $R_2$, $R_3$ or $R_4$ is a group of formula (II) or (III) and one of $R_5$, $R_6$, $R_7$ or $R_8$ is a group of formula (II) or (III);
$R_9$ and $R_{10}$ independently of each other are $C_1$-$C_4$alkyl or together with the C atom to which they are attached form a 5-membered, 6-membered or 7-membered carbocyclic ring;
$R_{11}$ is hydrogen, $C_1$-$C_4$alkyl, $C_5$-$C_7$cycloalkyl, 2-tetrahydropyranyl or $Si(C_1$-$C_4alkyl)_3$;
$R_{12}$ and $R_{13}$ independently of each other are $C_1$-$C_4$alkyl, $C_2$-$C_{12}$alkenyl, phenyl-$C_1$-$C_4$alkyl, phenyl-$C_1$-$C_4$alkyl which is substituted by $C_1$-$C_4$alkyl, or $R_{12}$ and $R_{13}$ together with the C atom to which they are attached form a 5-membered, 6-membered or 7-membered carbocyclic ring;
$R_{14}$ and $R_{15}$ independently of each other are $C_1$-$C_4$alkyl, $C_5$-$C_7$cycloalkyl, or together with the N atom to which they are attached form a 5-membered, 6-membered or 7-membered ring, which may contain additional heteroatoms O, S or N;
$R_{16}$ and $R_{17}$ independently of each other are hydrogen, $C_1$-$C_8$alkyl, $C_5$-$C_7$cycloalkyl, phenyl-$C_1$-$C_4$alkyl, phenyl or together with the C atom to which they are attached form a 5-membered, 6-membered or 7-membered ring;
provided that;
(1) compounds wherein $R_2$ is a group of formula (III) and $R_{14}$ and $R_{15}$ together with the N atom to which they are attached form a 6-membered ring, which contains an additional heteroatom O, X is a direct bond and Y is O; and
(2) compounds wherein $R_2$ is a group of formula (III) and $R_{14}$ and $R_{15}$ together with the N atom to which they are attached form a 6-membered ring, which contains an additional heteroatom O and X and Y are S; and
(3) compounds wherein $R_7$ is a group of formula (III) and $R_{14}$ and $R_{15}$ together with the N atom to which they are attached form a 6-membered ring, which contains an additional heteroatom O and X and Y are S; are excluded.

2. A photopolymerizable composition according to claim 1, where in the photoinitiator compound of formula (I):
one of $R_1$, $R_2$, $R_3$ or $R_4$ and one of $R_5$, $R_6$, $R_7$ or $R_8$ is a group of the formula (II); or
one of $R_1$, $R_2$, $R_3$ or $R_4$ and one of $R_5$, $R_6$, $R_7$ or $R_8$ is a group of the formula (III).

3. A photopolymerizable composition according to claim 1, where in the photoinitiator compound of formula (I):
X is S, a direct bond or $CR_{16}R_{17}$;
Y is O or S;
$R_1$, $R_3$, $R_4$, $R_5$, $R_6$ and $R_8$ are hydrogen;
$R_2$ and $R_7$ are a group of the formula (II) or (III);
$R_9$ and $R_{10}$ are $C_1$-$C_4$alkyl;
$R_{11}$ is hydrogen;
$R_{12}$ and $R_{13}$ are $C_1$-$C_4$alkyl;
$R_{14}$ and $R_{15}$ are $C_1$-$C_4$alkyl; and
$R_{16}$ and $R_{17}$ are hydrogen or $C_1$-$C_8$alkyl.

4. A photopolymerizable composition according to claim 1, which additionally to the component (B) comprises:
 (x) at least one further photoinitiator (C);
 (xi) at least one further coinitiator (D);
 (xii) at least one other additive (D); or
 (xii) a combination of (x) and (xi) or a combination of (x) and (xii) or a combination of (x) and (xi) and (xii).

5. A photopolymerizable composition according to claim 1, which comprises 0.05 to 15% by weight, of the photoinitiator compound of formula (I) based on the total composition.

* * * * *